US00PP31987P2

(12) United States Plant Patent
Hansen

(10) Patent No.: US PP31,987 P2
(45) Date of Patent: Jul. 14, 2020

(54) ***HEUCHERA* PLANT NAMED 'TIMELESS TREASURE'**

(50) Latin Name: ***Heuchera* hybrid**
Varietal Denomination: Timeless Treasure

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 21 days.

(21) Appl. No.: 16/350,856

(22) Filed: Jan. 24, 2019

(51) Int. Cl.
*A01H 5/02* (2018.01)
*A01H 6/80* (2018.01)

(52) U.S. Cl.
USPC ..... Plt./440

(58) Field of Classification Search
USPC ..... Plt./440
CPC ... A01H 5/02; A01H 5/12; A01H 5/00; A01H 5/025; A01H 6/80; A01H 6/14
See application file for complete search history.

(56) References Cited

U.S. PATENT DOCUMENTS

PP24,547 P3 * 6/2014 Egger ..... A01H 5/02 Plt./440

OTHER PUBLICATIONS

Germania Seed Walters Gardens Bare Root and Plug Perennials 2019, retrieved on Sep. 24, 2019, retrieved from the Internet at https://www.germaniaseed.com/pdf/2019/749_walters.pdf, pp. 1,13,24. (Year: 2019).*

Park Seed Walter's Gardens 2019, retrieved on Sep. 24, 2019, retrieved from the Internet at https://parkseed.com/images/ART/WALTERS%202019.pdf, 2 pages total. (Year: 2019).*

* cited by examiner

*Primary Examiner* — June Hwu

(57) ABSTRACT

The new and distinct hybrid of *Heuchera* plant named 'Timeless Treasure' with many small to medium-sized, shallowly lobed, glossy leaves with rounded apices and lobes. Tightly-branched, upright, burgundy flower stems are repeatedly produced from early summer to early fall for about fourteen weeks displaying large, rosy-pink flowers. The new plant has a compact, herbaceous perennial habit with mounds of leaves beginning the season purplish-red and developing a light silvery-gray overlay between the greyed purple surrounding the veins. It is vigorous and produces showy flowers over a long season, effective as a specimen plant, en masse in the landscape, or as a container plant.

1 Drawing Sheet

Botanical denomination: *Heuchera* hybrid.
Variety denomination: 'Timeless Treasure'.

STATEMENT REGARDING PRIOR DISCLOSURES UNDER 37 CFR 1.77(B)(6)

The first public disclosure of the claimed plant, in the form of a website to the public and email release to customers, was made by Walters Gardens, Inc. on Feb. 1, 2018 followed by the Walters Gardens, Inc. Summer 2018-Spring 2019 catalog. The first public sales of *Heuchera* 'Timeless Treasure' was by Walters Gardens, Inc. on Apr. 24, 2018. Walters Gardens, Inc. obtained the new plant and information about the new plant directly from the inventor. No plants of *Heuchera* 'Timeless Treasure' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of Coral Bells in the Saxifragaceae family and given the cultivar name of *Heuchera* 'Timeless Treasure'. 'Timeless Treasure' was hybridized by the inventor on Jan. 30, 2012 at a wholesale perennial nursery in Zeeland, Mich., USA. The seed or female parent was a proprietary, unreleased proprietary hybrid known as 11-98-1 (not patented) and the pollen or male parent was a proprietary unreleased hybrid known as K11-52-16 (not patented).

*Heuchera* 'Timeless Treasure' was first selected in the fall of 2014 and passed final evaluation in the fall of 2016 from among many other seedlings from the same cross and hundreds of other crosses and assigned the breeder code 12-144-8 through the remaining evaluation process. *Heuchera* 'Timeless Treasure' has been asexually propagated initially by basal cuttings at the same nursery in Zeeland, Mich. in 2014and later by sterile, shoot-tip, tissue culture propagation, and the resultant plants have remained stable and continued to exhibit the same characteristics as the original plant for multiple generations.

BRIEF SUMMARY OF THE INVENTION

The nearest comparison varieties include: the female parent 11-98-1, 'Grape Expectations' U.S. Plant Pat. No. 26,894, 'Berry Timeless' U.S. Plant Pat. No. 26,357, 'Peppermint' U.S. Plant Pat. No. 24,563, 'Frost' U.S. Plant Pat. No. 24,547, 'Petite Marbled Burgundy' U.S. Plant Pat. No. 11,059, Petite Pearl Fairy U.S. Plant Pat. No. 11,058 and 'Grape Timeless' copending U.S. Plant patent application Ser. No. 16/350,864. 'Grape Expectations' has flowers that are creamy white for a shorter season and the foliage is larger. 'Berry Timeless' has a similar profusion of flowers throughout the season but the flower color is lighter pink and the foliage is light green with slight silvering between the veins. 'Peppermint' has similar habit, leaf size and flower period but the flowers are pale pink and the foliage is medium green with silvering between the veins. 'Frost' has more pointed foliar lobes, has white flowers on much shorter stalks with fewer flowers per stalk. 'Petite Marbled Burgundy' has less purple in the foliage and the flowers are smaller and creamy white. 'Petite Pearl Fairy' has more green and less purple and silver in the foliage and the flowers are smaller and creamy white. 'Grape Timeless' has shorter flower stems and smaller, lighter pink flowers, and the foliage is larger with more purple and less silver. The female parent, 11-98-1, has small caramel-color leaves with near white flowers. The male parent has foliage with more greenish color and the flowers are produced over a shorter period on taller stalks. *Heuchera* 'Timeless Treasure' differs from its parents as well as all other coral bells known to the applicant in the following combined traits:

1. The small to medium-sized, flat, glossy foliage has rounded apices and lobes.
2. Leaf blades emerge purplish-red and develop a glossy, light, silvery-gray with greyed-purple area surrounding the veins.
3. Leaf blades are shallowly dissected with apices rounded and mucronulate.
4. Flowers are large, outwardly-facing, rosy-pink on dark-purple stems.
5. Flowering period begins in early summer and continues for about fourteen weeks into early fall with repeat panicles.
6. Compact, short, heavily-branched, burgundy panicles display flowers at multiple nodes beginning under foliage.
7. The new plant is vigorous and produces compact clumps and many small to medium-sized individual leaves.

BRIEF DESCRIPTION OF THE DRAWINGS

The photographs of *Heuchera* 'Timeless Treasure' demonstrate the overall appearance of the plant including the unique traits of a plant in a full sun trial block in Zeeland, Mich. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
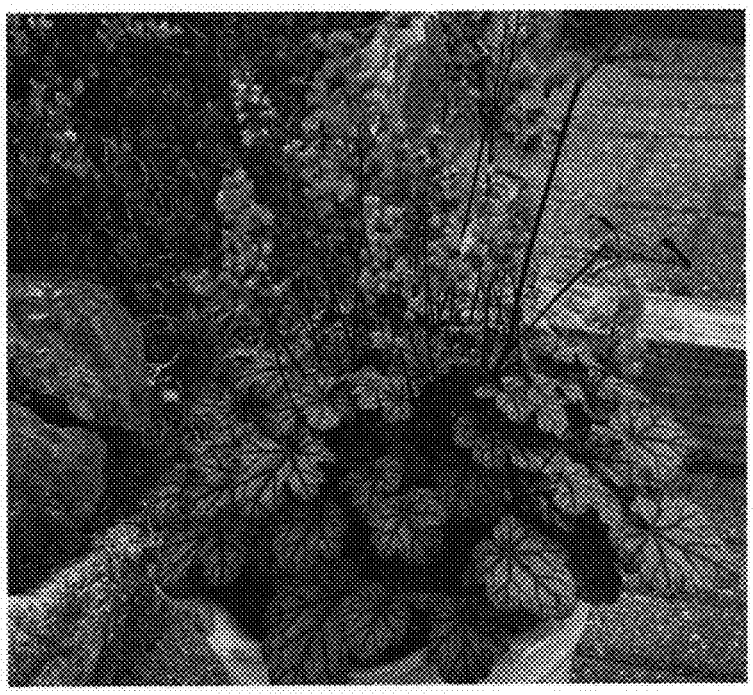
FIG. 1 shows a two-year-old plant grown in a container in a partially shaded greenhouse in peak flowering season.
Figure 2:
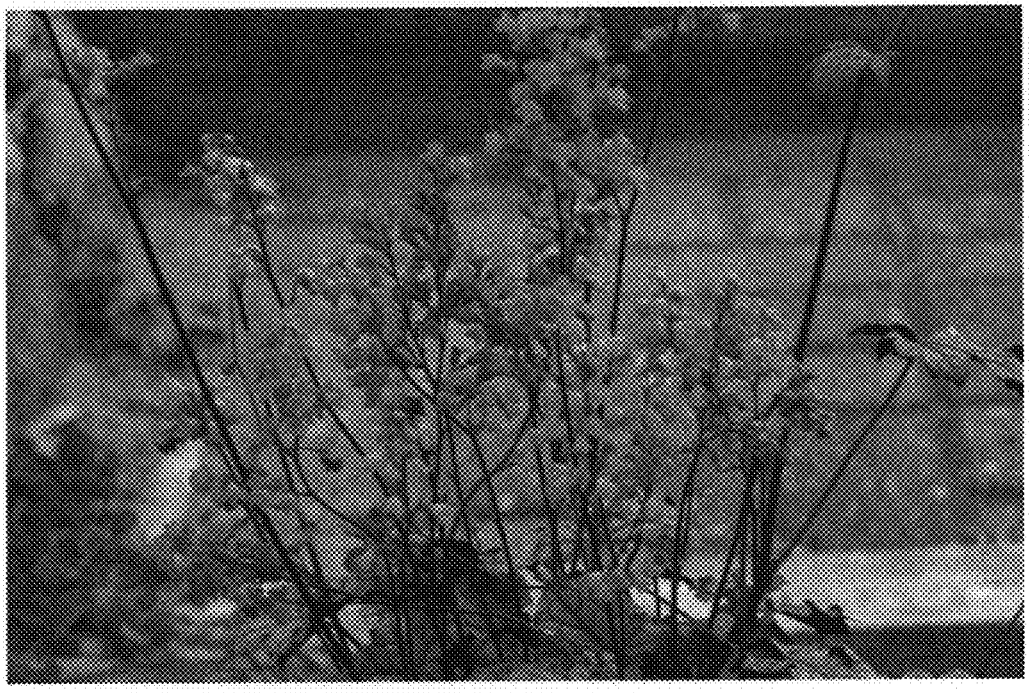
FIG. 2 shows a close-up of a flower panicle with buds and flowers from a two-year-old plant.

The following description is based on two-year-old plants growing in a partially shaded greenhouse in Zeeland, Mich., USA. The new plant has not been grown under all possible environments and may phenotypically appear different under different conditions such as light, temperatures, fertilizer, and water, without any difference in genotype. The color descriptions used are from the 2015 edition of The Royal Horticultural Society Colour Chart except where common dictionary terms are used.

Parentage: Female or seed parent was 11-98-1, a selection of a cross between 'Caramel' U.S. Plant Pat. No. 16,560 and a proprietary selection of *Heuchera parishii*; the male or pollen parent was the proprietary unreleased hybrid known only by the breeder code K11-52-16, a selection from the cross between 'Mocha Mint' (not patented) times 'Milan' U.S. Plant Pat. No. 21,682;

Plant habit: Hardy herbaceous perennial with basal rosette of foliage; mounded foliage about 28.0 cm tall and 48.0 cm in diameter with scapes to about 50.0 cm long; with about 6 branched stems per plant to about 14.0 cm long and 1.5 cm diameter at base, about 3 branches per stem, with about 25 to 40 leaves per branch; about 32 scapes during peak flowering;

Roots: Fibrous, finely branched;

Growth rate: Rapid, rooting from cutting in two weeks and finishing in three-liter container in about two and a half months;

Foliage: Cordate to nearly rounded; micro-puberulent adaxial and abaxial; palmately shallowly lobed with five main lobes shallowly dissected, less than one-quarter of the distance to the petiole; each main lobe with up to three very shallowly indented sub-lobes; apex and lobe apices rounded and mucronulate; base cordate with basal lobes nearly overlapping to overlapping about 0.5 cm; margins crenate to mucronulate, ciliolate; lustrous adaxial and abaxial; held nearly horizontal; margin mostly flat;

Leaf blade size: To about 10.0 cm wide and 9.5 cm long, average about 9.0 cm wide and 9.0 cm long;

Leaf color: Spring and young emerging adaxial between RHS N186C and RHS N186D between veins and area surrounding veins nearest RHS N186B; spring young emerging abaxial nearest RHS 187B; mature mid-season adaxial nearest blend between RHS N187B, RHS 202B and RHS 202C with a slight blush of nearest RHS 186C between the veins and surrounding the veins nearest RHS N187A; abaxial mature mid-season nearest RHS 187A; fall and winter adaxial nearest blend between RHS 198C and N187B with portion surrounding veins nearest RHS 137A; abaxial fall and winter between RHS N186C and RHS 187A;

Leaf quantity: Dense, about 300 per plant;

Veins: Palmate; sparsely hirsutulous and costate abaxial, glabrous and nearly flat adaxial;

Vein color: Emerging or early spring adaxial nearest RHS 180C and abaxial nearest RHS 185C; mid flowering season adaxial blend of nearest RHS 195B and RHS 173C, mid flowering season abaxial nearest RHS N170D; late season adaxial variable, nearest RHS 146D proximally and nearest RHS 137A distally;

Petiole: Cylindrical, base amplexicaul; micro-puberulent with hairs to less than 0.1 mm long; to about 14.0 cm long and 4.0 mm wide above stipule; average about 13.0 cm long and about 3.0 mm diameter above stipule;

Petiole color: Emerging leaf nearest RHS 187C; flowering season mature leaf nearest RHS N186C with green undertones of nearest RHS 146C; late season nearest RHS 148A;

Stipule: Flared at base of petiole; glaucous abaxial and adaxial; margin ciliate; to about 2.0 cm long and about 12.0 mm wide at base; with two lateral projections of about 5.0 mm long and 2.0 mm across in distal portion;

Stipule color: Young expanding adaxial and abaxial nearest RHS 164B toward center and nearest RHS 164D along margins; mature adaxial and abaxial nearest 186A toward center and nearest RHS 146D toward margin;

Peduncle: Panicle; cylindrical; stiff; pubescent; upright; densely branched; to about 50.0 cm long and 4.0 mm diameter at base, average about 47.0 cm tall and 3.5 mm diameter; about 40 per plant with up to about 120 flowers per panicle, average about 100; initial flowers under foliage; tightly-branched panicle with up to 18 branches up to 11.0 cm long and 1.0 mm diameter decreasing distally, average 15 branches per panicle; lower branches mostly upright becoming outwardly distally; each branch subtended by foliar bract; flower density moderate;

Peduncle color: Nearest RHS N186C with undertones of nearest RHS 146C;

Foliar bract: Oblong palmate; incised margins to deeply lobed; apex acute; truncate clasping base; to 1.4 cm long and 1.0 cm across, decreasing distally; sessile;

Foliar bract color: Adaxial and abaxial nearest RHS 186C distally and nearest RHS N186D proximally;

Flowering longevity: Panicle effective for about two to four weeks; individual flowers about 5 days; self-cleaning;

Flowering period: Beginning early summer and repeating with new panicles without the need to remove old panicles through early fall for about 14 weeks;

Pedicel: Cylindrical; puberulent; to about 5.0 mm long and 0.5 mm diameter, average about 4.0 mm long and 0.5 mm diameter; attitude outwardly;

Pedicel color: Nearest RHS 187C;

Buds one day prior to opening: Ellipsoidal; rounded apex and attenuate base; puberulent to glandular; about 6.0 mm long and 3.0 mm diameter;

Bud color one day prior to opening: Nearest RHS 184C;

Flower: Perfect; campanulate; actinomorphic; about 7.0 mm long and 10.0 mm in diameter at corolla face;

Flower attitude: Outwardly;

Calyx: Base fused in proximal 4.0 mm to form hypanthium; puberulent to glandular abaxial, glabrous adaxial; about 8.0 mm long and 9.0 mm wide at apex;

Sepals: Five; lanceolate; acute apex, fused in basal 4.0 mm; to about 8.0 mm long and 3.0 mm wide at fusion;

Sepal color: Abaxial nearest RHS 185B, adaxial nearest RHS 184C with slight undertone of nearest RHS 146D toward apex;

Petals: Five; oblanceolate to spatulate; subacute apex and attenuate base; margin entire; glabrous adaxial and abaxial; about 3.5 mm long and 1.3 mm wide in middle;

Petal color: Abaxial and adaxial between RHS 70C and RHS 70D;

Androecium: Five adnate to adaxial sepal about 1.0 mm above base;

*Filaments*.—Five, thin, glabrous; about 1.0 mm long and about 0.3 mm diameter; color nearest RHS NN155B.

*Anthers*.—Ellipsoidal, distinct, basifixed, longitudinal; about 1.0 mm long and about 0.5 mm across; color nearest RHS 18B.

*Pollen*.—Has not been observed;

Gynoecium: One, two-beaked; half-inferior; bifid style with pistil split at ovary; about 7.0 mm long;

*Style*.—Bifid; split apart at apex of ovary; about 3.0 mm long and about 0.5 mm diameter; color nearest RHS 63A.

*Stigma*.—Acute apex, about 0.3 mm diameter; color nearest RHS 186D.

*Ovary*.—Half-inferior, about 3.5 mm long and 2.0 mm diameter; ellipsoidal to globose; acute apex and base rounded; color lighter than RHS 160B.

Fruit: Not yet observed;

Seeds: Not yet observed;

Disease and pest tolerance: The new plant grows best with ample moisture and drainage in either part sun or full shade. Cold hardy from USDA zones 4 to 9. Other resistance and tolerance outside of that normal for *Heuchera* is not known.

It is claimed:

1. The new and distinct Coral Bells plant named *Heuchera* 'Timeless Treasure' as herein described and illustrated.

* * * * *